United States Patent [19]

Roussel

[11] Patent Number: 4,506,962
[45] Date of Patent: Mar. 26, 1985

[54] CONTACT LENS FOR OBSERVATION OR IRRADIATION OF THE EYE

[75] Inventor: Philippe Roussel, Wassenaar, Netherlands

[73] Assignee: LASAG AG, Thun, Switzerland

[21] Appl. No.: 406,930

[22] PCT Filed: Feb. 8, 1982

[86] PCT No.: PCT/CH82/00018
§ 371 Date: Aug. 10, 1982
§ 102(e) Date: Aug. 10, 1982

[87] PCT Pub. No.: WO82/02656
PCT Pub. Date: Aug. 19, 1982

[30] Foreign Application Priority Data
Feb. 12, 1981 [CH] Switzerland ............................ 931/81

[51] Int. Cl.³ ........................... A61B 3/00; G02C 7/04
[52] U.S. Cl. ................................. 351/160 R; 351/219; 351/221
[58] Field of Search ............. 351/219, 221, 160 R–162

[56] References Cited

U.S. PATENT DOCUMENTS 3,589,800 6/1971 Cardona .................... 351/160 R X
3,630,602 12/1971 Herbert ....................... 351/160 R X
4,033,679 7/1977 Sussman ........................ 351/219 X

FOREIGN PATENT DOCUMENTS 30210 6/1981 European Pat. Off. .
2248814 5/1975 France .
2049216 4/1980 United Kingdom .

Primary Examiner—John K. Corbin
Assistant Examiner—Scott J. Sugarman
Attorney, Agent, or Firm—Peter L. Berger

[57] ABSTRACT

The invention concerns contact lenses for observation or irradiation of the eye. The contact lens contains, for useful radiation, an entry face (1), a surface (2) reflecting by total reflection and an approximately spherical exit surface (3). Entry face (1) constitutes a wave surface for useful radiation.

10 Claims, 4 Drawing Figures

CONTACT LENS FOR OBSERVATION OR IRRADIATION OF THE EYE

BACKGROUND OF THE INVENTION

This invention concerns a contact lens for observation or irradiation of the eye.

Contact lenses of various types are used in opthalmology for observation or treatment of the eye by irradiation, notably, for treatment of the anterior chamber of the eye.

The contact lenses most often used to date have been the Koeppe contact lens and the Goldman type contact lens. The use of such lenses was described, in particular, in the published work entitled "Gonioskopie und Goniofotographie" by Winfried Muller and Hans-Peter Brandt, Ferdinand Enke Verlag Stuttgart 1979.

The Koeppe contact lens is a lens having a convex beam entry face and an approximately spherical exit face designed to be applied to the transparent zone of the cornea. Those lenses, however, have so far been used only for observation of the eye. The size of those lenses was primarily designed to obtain an image of the anterior chamber of the eye with a magnification factor of 20 to 30 in the course of the observation procedures.

The Goldmann type contact lens contains essentially one flat radiation entry face, one approximately spherical exit face designed to be applied to the transparent zone of the cornea and at least one reflecting face or wall making possible indirect observation of the anterior chamber of the eye by total reflection of the beams on that wall.

In spite of their undeniable intrinsic qualities for observation procedures, such as manageability, ease and convenience of use for the ophthalmologist, as far as the Goldmann type contact lens is concerned, those two types of lenses do not allow for treatment of the eye by irradiation with guaranteed safety for the patient, reliability and reproducibility of treatment, especially with high-energy irradiation by laser beam. In fact, in that type of treatment, one essential objective is to obtain a sufficient energy density to produce, by optical breakdown of the dielectric medium inside the eye, a pressure wave capable of assuring perforation of adjoining walls of the anterior chamber of the eye. However, patient safety factors in the course of those treatments demand a maximum reduction of the radiated energy density at the cornea-contact lens junction in order to prevent injury by the latter in the zone of entry of the laser beam into the eye. Furthermore, in order to assure, on each laser pulse firing, conditions of reproducibility and stability of emission of the pressure wave (shock wave) in the eye, it is indispensable for the contact lens, by its qualities of shape and composition, to afford the best possible focusing of the useful laser beam and the maintenance of its focussing qualities for any point of the eye and, mainly, of the anterior chamber of the eye.

The contact lenses of the prior art do not provide all of the conditions necessary for a reliable, safe and consistent treatment. In particular, it has been verified that the use of Goldmann type contact lenses, as previously described, does not make it possible, under some conditions of use, i.e., definitely, for certain points of the anterior chamber, to obtain sufficient energy at the focusing point to produce, by optical breakdown, emission of the desired pressure wave. In fact, the optical breakdown phenomenon for these points is likely to be obtained only at the cost of a substantial increase of radiated energy density of the beam, that increase, by a factor of at least 2 to 3, being prohibitive, due to the risks of injury to the cornea and damage to the contact lens itself.

This invention makes it possible to remedy those problems and involves the use of a contact lens for observation and treatment of the anterior chamber of the eye.

Another object of this invention is to provide a contact lens which enables by laser irradiation of the eye through that lens, to obtain the optical breakdown and pressure wave phenomenon of the medium inside the eye with energy radiated by the beam that is as low as possible.

Another object of this invention is to provide a contact lens enabling an optical breakdown phenomenon that is stable and well localized spatially, that same contact lens enabling appreciably identical effects to be obtained, from the clinical standpoint, for identical parameters of laser emission.

A further object of this invention is to provide a contact lens, for which all of the above-mentioned characteristics must remain appreciably constant, regardless of the firing point in the eye or, for a fixed firing point, regardless of the relative positions of the laser beam and of the contact lens in relation to the eye.

The contact lens according to the invention comprises for useful radiation, an entry face, a surface reflecting by total reflection and an approximately spherical exit surface, characterized in that the entry surface constitutes, for useful radiation, a wave surface.

Such contact lenses can be used in eye surgery, notably, for the diagnosis and treatment of conditions such as glaucoma or cataracts. For further details on this subject, one can refer to European patent application No. 80 810 357.6 and American patent application No. 211,207 now U.S. Pat. No. 4,409,979 and Ser. No. 211,202 now U.S. Pat. No. 4,391,275 in the applicant's name.

The invention will be described in detail by means of the specification and drawings below, in which the same references represent the same elements and where:

Figure 1A:
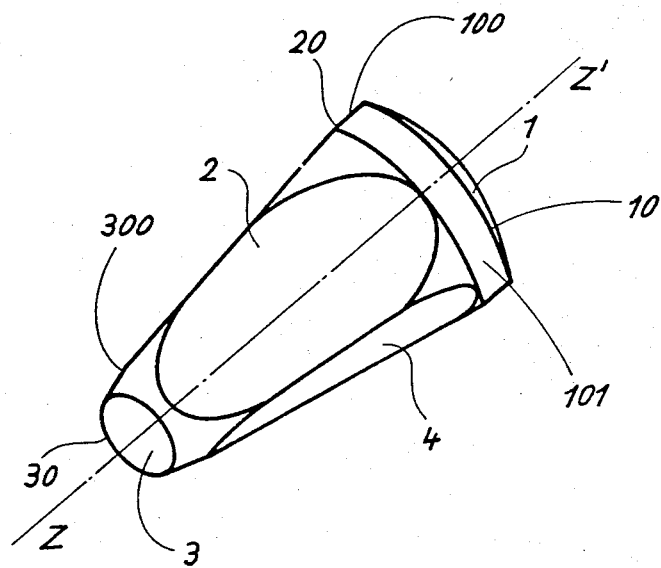
FIG. 1a is a perspective view of a contact lens according to the invention.
Figure 2:
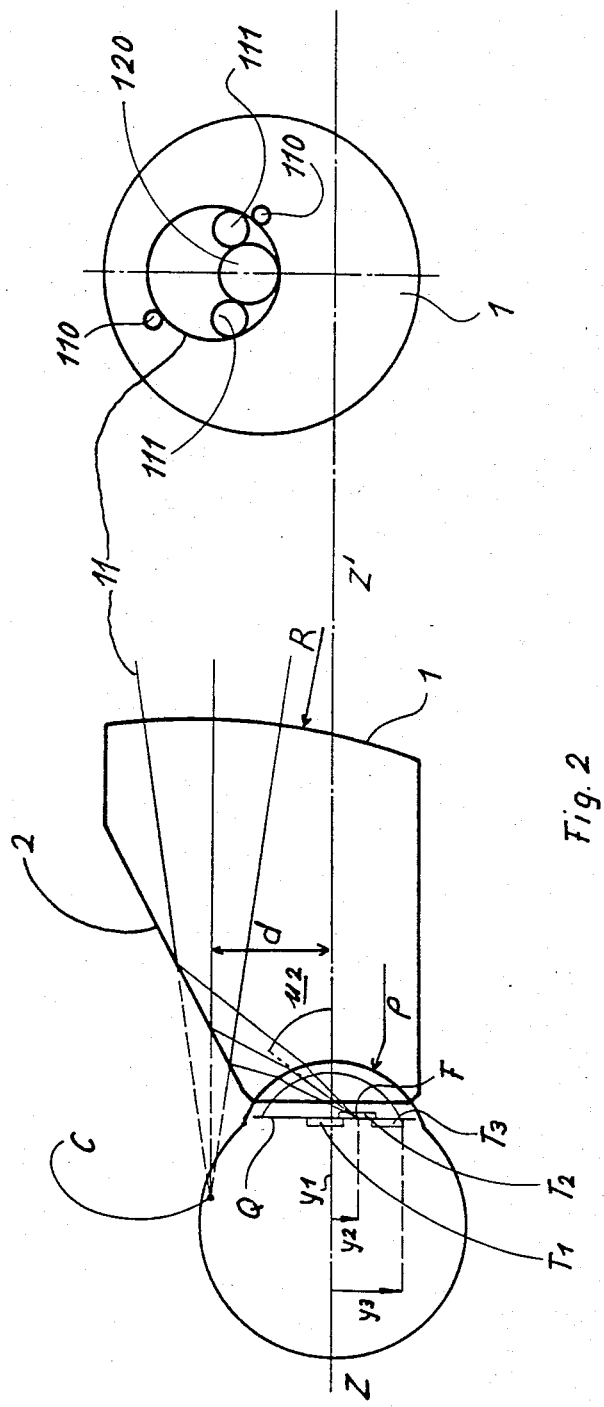
Figure 3:
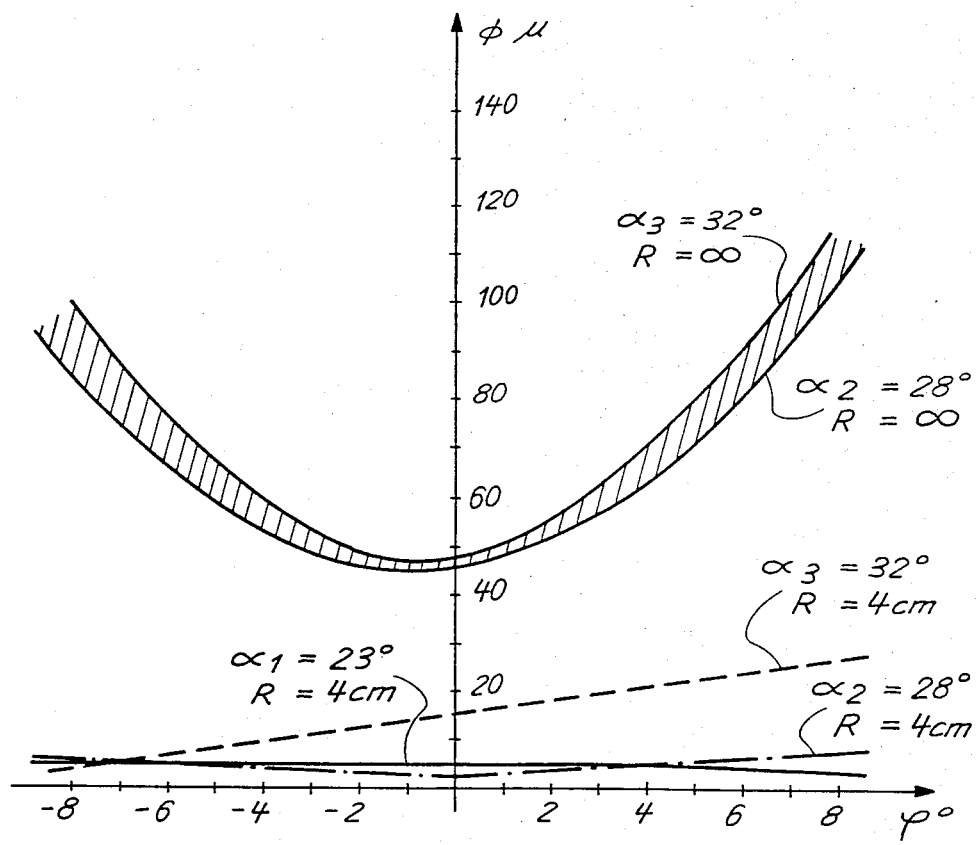

FIG. 2 also is a sectional view along a longitudinal plane of symmetry of the contact lens of FIG. 1a applied against the cornea of an eyeball and the image of the useful beam on the entry face of the contact lens is also shown;

FIG. 3 represents, by way of comparative result, the aberration and focusing curves of a useful beam in the case of use of a Goldmann type contact lens and for a contact lens according to the invention.

DETAILED DESCRIPTION

In accordance with FIG. 1a, the contact lens for observation or irradiation of the anterior chamber of the eye comprises, for useful radiation, an entry face 1, a face 2 reflecting by total reflection of that radiation and an approximately spherical exit surface 3. The contact lens, as represented on FIG. 1, is applied directly to the transparent zone of the cornea, the approximately spherical exit surface 3 being applied to the cornea. A bonding product of the kind known by the trade name "Methocel" makes it possible to assure a good bond between the contact lens and the cornea. In order to diminish the aberrations of the focusing point of the beam to the utmost, entry surface 1 constitutes a wave surface for the useful radiation. Thus, at the air-contact lens interface formed by entry surface 1, the useful radiation undergoes no deviation, the distribution of light energy from the useful beam on the wave surface being totally maintained. The useful beam is to be interpreted as the convergent laser treatment beam, the angle of the focusing cones being approximately 16°, or any combination of beams making possible visualization of the path of the treatment laser beam by the ophthalmologist, or illumination and observation of any point of the anterior chamber of the eye to be observed. For further details on the formation of useful radiation, reference may be made to the aforesaid patent applications in the applicant's name.

Figure 1B:
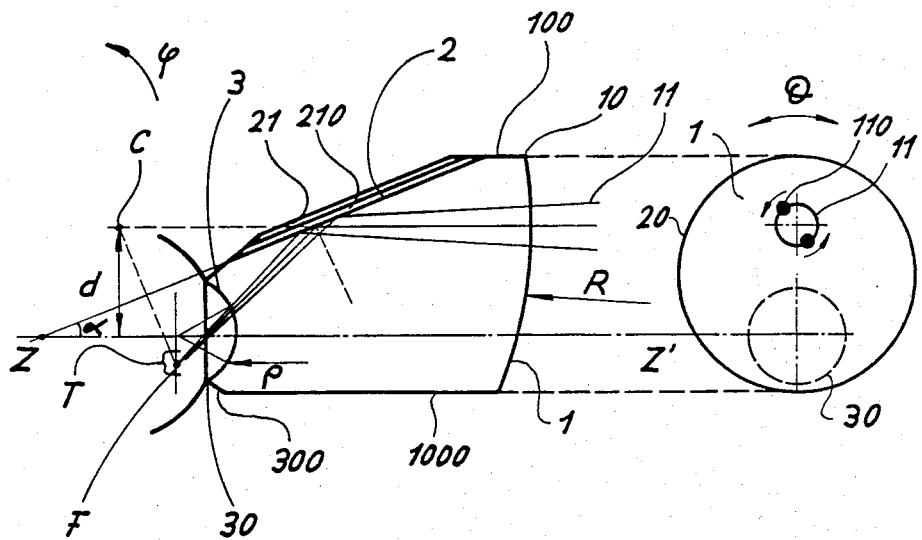
FIG. 1b is a sectional view along a longitudinal plane of symmetry of the contact lens of FIG. 1a applied against the cornea of an eyeball for observation and treatment of the anterior chamber of the eye.

As represented on FIGS. 1a and 1b, the wave surface constituting useful radiation entry face 1 is a spherical surface, the center of curvature C of which is the image, in the lens and after reflection on reflecting surface 2, of theoretical point F of the eye to be irradiated. As represented, notably, on FIG. 1a, the contact lens is made of a material transparent to useful radiation, roughly delimited by a shape having a longitudinal plane of symmetry. The shape consists substantially of a cylindrical surface of revolution 100. The cylindrical surface of revolution 100 may be replaced by a conical surface having the same longitudinal plane of symmetry as that for the cylindrical surface. Spherical entry surface 1 has a small circle 10 as a directrix of cylindrical surface 100 or of the conical surface. In case the shape of the lens consists of a cylindrical surface 100, small circle 10 of spherical entry surface 1 constituting a directrix of cylindrical surface 100 forms an ellipse on the latter. Spherical exit surface 3 of useful radiation forms for the axis of symmetry, contained in the longitudinal plane of symmetry of the contact lens, a line ZZ' parallel to a generatrix 1000 of cylindrical surface 100. Exit surface 3 further includes a small circle 30 having a radius less than that of director circle 20 of cylindrical surface 100, circle 30 being offset from circle 20. On FIG. 1b the image of useful radiation entry face 1 is delimited by director circle 20 of cylindrical surface 100 with small circle 30 of exit surface 3 being represented, offset, by a chain-dotted line. The useful radiation consists, for example, of a treatment beam 11, whose image on entry face 1 is represented, the treatment beam being accompanied by two rotating visualization beams 110 tangent to the envelope of beam 11 and enabling the practitioner to form the envelope of treatment beam 11.

Spherical entry face 1 and exit face 3 constitute, for the contact lens, a convex surface and a concave surface respectively.

The contact lens is used by the physician by pressing the lens on the elastic cornea. It can be assumed that the anterior surface of the cornea on laser irradiation is spherical and has the same radius of curvature as the corneal face of the lens formed by exit surface 2. The radius of curvature $\pi$ of concave spherical surface 3 is approximately equal to 0.8 cm. That value, greater than the radius of curvature of the anterior face of the cornea of an eye at rest, makes it possible to form a good contact between the lens and cornea by the elimination of air bubbles. Also, it affords the opportunity, on observation of the iridocorneal angle, to widen that angle by pressure of the lens on the eye. The risk of formation of Decemet's folds can be avoided by movement of the contact lens. The surface 2 reflecting by total reflection is a flat surface formed by the intersection of a plane and of cylindrical surface 100 or of the conical surface. As represented on FIG. 1b, that plane forms, with a plane containing the axis of zymmetry ZZ' of exit surface 3 and at right angles to the longitudinal plane of symmetry of the contact lens, a dihedral angle $\alpha$ ranging between approximately 18° and 48°. That plane containing the axis of symmetry ZZ' and at right angles to the longitudinal plane of symmetry of the contact lens is represented on FIG. 1b by its intersection with axis ZZ'. Also represented on FIG. 1a are faces 4, which are formed by the intersection of a plane and the cylindrical surface 100 or a conical surface. Those faces 4 make it possible, by removal of material from the cylinder or cone, to lighten the contact lens. There may be other means to lighten the contact lens that will be obvious to one of ordinary skill in the art. The material used for making the lens is preferably a material which does not shrink after thermal stress, e.g., a BK7 type lens.

As represented on FIG. 1b, the surface 2 reflecting by total reflection contains a protective plate 21 creating, between reflecting surface 2 and plate 21, an air gap 210 assuring the condition of total reflection for useful radiation 11. That plate makes possible protection against the projections on reflecting surface 2 of liquids such as "Methocel," which would be capable of impairing the conditions of total reflection and energy density of the treatment laser beam. Plate 210 is cemented, for example, with a thermosetting resin. The center of curvature C of the spherical entry face of useful radiation 11 is situated in the longitudinal plane of symmetry of the contact lens at a distance d of close to 1 cm from the axis of symmetry ZZ' of exit surface 3 of the contact lens.

That characteristic makes it possible to standardize the dimensions of the contact lens and enables it to be made more easily.

The contact lens further contains a shoulder 101 at small circle 10 of radiation entry face 1 and a shoulder 300 at small circle 30 of exit surface 3. Shoulder 101 consists of free cylindrical surface 100 and shoulder 300 comprises a surface bordered by cylindrical surface 100 and a conical bottom portion. Shoulders 101 and 300 make it possible to surround the contact lens with a protective plastic case facilitating handling of the lens in azimuth $\pi$ in rotation $\theta$ around the axis of symmetry ZZ' by the physician in the course of observation and treatment.

Thus, for a given value of the dihedral angle $\alpha$ and for a range of values of relative incidence of useful radiation 11 on entry face 1 of the contact lens obtained by rotation of the lens in azimuth $\psi$, and by rotation $\theta$ of the contact lens around the axis ZZ', the focusing point F of the radiation enables a zone of treatment T approximately in the shape of a circular ring centered on axis ZZ' to be formed in the eye.

As represented on FIG. 2, the anterior face of the iris is assimilated on first approximation to the plane tangent Q to the anterior face of the crystalline lens and perpendicular to the axis ZZ' merged on FIG. 2 with the optical axis of the eye. The geometric parameters of the eye are, for the cornea, in the presence of the contact lens:

| | |
|---|---|
| radius of curvature of the anterior face of the | 0.8 cm |

```
-continued
cornea
thickness                                                    0.5 mm
radius of curvature of the posterior face                    0.75 cm
For a laser emission wavelength
λ = 1.06μ, laser Nd:YAG, the index of the cornea
is n = 1.377,
index of the aqueous humor n = 1.337, those values
being obtained from Tagawa's curves
(Tabulae biologicae).
```

Taking into account the different diseases to be treated, the laser firings must be carried out in the iridocorneal angle, on the iris, on the crystalline lens and in the vicinity of the plane Q tangent to the anterior surface of the crystalline lens situated at approximately 3.6 mm from the anterior face of the cornea. Strictly speaking, for each point situated in that plane at a fixed distance from the axis of the eye, there is a value of $\alpha$, taking into account the choice of the parameter d distance from the center of curvature C of the entry face to axis ZZ' and, therefore, the distance from the axis of the useful beam to that same axis, making it possible to focus the beam on that point under optimal focusing conditions.

However, bearing in mind the dispersions of the value of said parameters as a function of the individuals, it is sufficient to define a given number of zones of treatment on that plane Q which, considering the freedom of handling of the practitioner, can each be obtained without appreciable deterioration of focusing qualities by means of a contact lens of given characteristics. On FIG. 2, three zones of treatment T1, T2 and T3, have been defined with adjacent zones overlapping. The median line of those zones, circumference of respective radius y1, y2, y3, corresponds to a middle zone. The choice of radii $y_1=0$, $y^2=2.23$ mm and $y^3=5.6$ mm was carried out with a view to making possible an optimum inclination of the useful beam after reflection on reflecting face 2, taking into account the mean distance d, (axis of useful beam 11 - axis ZZ'). That inclination u from axis ZZ', for a beam focusing cone of approximately 16°, makes it possible, substantially, to obtain a maximum mechanical penetration efficiency, because the beams in the vicinity of plane Q are as close as possible to normal in that zone in keeping with the topography of the zone to be treated. This mechanical efficiency is, furthermore, combined with a maximum optical path of the beam in the eye, the primary consequence of which is to impose a minimum energy density of radiation at the anterior face of the cornea, cornea-lens junction, and, therefore, to guarantee the patient's absolute safety. In addition, those values for firings on the crystalline lens allow firings which, nevertheless, avoid illumination of very sensitive parts of the retina, such as the fovea, for example. The corresponding inclination values are:

$u_1 = 49°$ central zone of the crystalline lens. That value furnishes a mean optical path for the beam of 4 mm. This relatively short path does not make possible pulse firings, the energy of which exceeds 30 to 40 mJ, due to the positional instability risks of the optical breakdown.

$u_2 = 63°$ intermediate zone corresponding mainly to treatment of the iris, that value furnishes a mean optical path of 5 to 6 mm and allows high-energy laser firings of 50 to 100 mJ.

All of the different parameters above enable a particular contact lens to be defined by zones of treatment, thus preferentially making possible the treatment of the corresponding zone. Then, for each zone T1, T2, T3 and for the corresponding parameters $y_1$, $u_1$; $y_2$, $u_2$; $y_3$, $u_3$, the dihedral angle $\alpha$ constituted by the plane delimiting the surface reflecting by total reflection and the plane at right angle to the longitudinal plane of symmetry of the lens and containing the axis of symmetry ZZ' of exit surface 3 of useful radiation is chosen among observable values $\alpha 1=23°$, $\alpha 2=28°$, $\alpha 3=32°$, corresponding respectively to the parameters $y_1$, $u_1$; $y_2$, $u_2$; $y_3$, $u_3$ previously defined.

The entry face of any contact lens thus obtained preferably contains a radius of curvature R approximately equal to 4 cm. Thus, as represented on FIG. 2, the image of a useful beam 11 formed, an observation, by rotating visualization beams 110, by treatment beam 11 last used by the practitioner, by observation beams 111 and 111' and by an illumination beam 120 exists without overlapping between observation and illumination beams, thus avoiding blinding of the practitioner by reflection of the illumination beam at the entry face 1. For further details on the composition of useful beam 11, reference can be made to the patent applications in the applicant's name already mentioned.

All three contact lenses thus defined constitute a set of contact lenses making it possible for the practitioner to achieve optimum observation or irradiation of the anterior chamber of the eye. Each of the lenses of the set has, as dihedral angle $\alpha$ formed by the plane delimiting the surface reflecting by total reflection and the plane perpendicular to the longitudinal plane of symmetry of the lens and containing the axis of symmetry ZZ' of the exit surface 3 of useful radiation with a different value equal to one of the three observable values. That set makes it possible to assure irradiation or observation of all of the points of the anterior chamber of the eye.

In accordance with FIG. 3, the curves represent the aberration $\phi$ in micrometers measured against increasing in diameter of a focusing spot of 60 μm for a beam, the focusing cone of which is approximately 16° as a function of the angle of incidence of useful beam 11 on reflecting face 2, the lens being subjected to a rotation in azimuth $\psi$, for the three contact lenses constituting the set according to the invention and for Goldmann type lens for which the radius of curvature of the entry face is infinite, $R = \infty$. The hatched zone corresponds to the dispersion of aberration for a flat entry face of the Goldmann lens type, as a function of the dihedral angle $\alpha$ of the plane constituting the reflecting surface and of the plane containing the axis ZZ' at right angles to the longitudinal plane of symmetry of the contact lens. It is easy to see that the maximum aberration produced by a contact lens according to the invention is very slight in relation to the diameter of the focusing spot and is approximately three times less, in the most unfavorable case, that is the $\alpha 3 = 32°$, case of the lens adapted to treatment of the iridocorneal angle, than in the case of a Goldmann type lens.

A system of contact lenses has thus been described for the laser beam observation or irradiation in which a major safety factor is attained for the patient. The great convenience of use for the practitioner must be added to that quality. In fact, the useful beam being approximately parallel to the optical axis of the eye, observation of all of the parts of the anterior chamber of the eye to be treated is accomplished without substantial change in the patient-physician position by mere handling of the contact lens. That handling can be accomplished by 360° rotation $\theta$ around the axis ZZ' of symmetry of the exit face 3 of the lens and by rotation in azimuth $\psi$ of the contact lens. The only limitation to be envisaged for the amplitude of rotation in aximuth $\psi$ is that of loss of the condition of total reflection on reflecting face 2. For each of the three lenses defined above, the amplitude of maximum rotation of the lens in the critical direction, that is, the direction tending to close the angle of incidence of useful beam 11 on reflecting surface 2, is

| | |
|---|---|
| $\Psi 1 = 17, 43°$ | for $\alpha 1 = 23°$ |
| $\Psi 2 = 12, 43°$ | for $\alpha 2 = 28°$ |
| $\Psi 3 = 8, 43°$ | for $\alpha 3 = 32°$ | for a BK7 lens of index 1.507 at $\lambda = 1.06\mu$.

Those limiting values of rotation in azimuth in relation to an initial starting position correspond approximately to the coincidence of the optical axis of the eye and the axis of symmetry ZZ' of exit surface 3. They are more than sufficient to enable the physician to compensate, by mere handling of the contact lens, for the erratic movement of the patient's eyeball, existing in spite of prior anesthesia of the eyeball muscles, or to reach, with appreciable impairment of the conditions of focusing the beam and, therefore, with assurance of reliability and reproducibility of the operations, each point of the corresponding zones of treatment respectively.

I claim:

1. In a contact lens for observing a point in an eye and irradiating said point with a convergent laser beam, said convergent laser beam comprising spherical wave surfaces, said contact lens comprising an entry face having an entry surface, a reflecting plane surface for totally reflecting said beam and an exit face having a substantially spherical concave exit surface, the improvement comprising said entry surface comprising a spherical surface, the center of curvature of which is the image of said point in said reflecting surface to form a wave surface for said beam, whereby said beam passes through said entry face undeviated.

2. The contact lens of claim 1, wherein said entry surface, said reflecting surface and said exit surface have one and the same plane of symmetry, and the plane of said reflecting surface forms a dihedral angle ranging substantially between 18° and 48° with a plane containing the symmetry axis of said exit surface and perpendicular to said plane of symmetry.

3. The contact lens of claim 2, further comprising a protective plate disposed parallel to said reflecting surface for enclosing an air gap between said protective plate and said reflecting surface, said air gap causing total reflection of said beam.

4. The contact lens of claim 2, wherein said exit surface has a radius of curvature substantially equal to 0.8 cm.

5. The contact lens of claim 2, wherein the center of curvature of said entry surface is situated substantially at 1 cm of the axis of symmetry of said exit surface.

6. The contact lens of claim 4, wherein the center of curvature of said entry surface is situated substantially at 1 cm of the axis of symmetry of said exit surface.

7. The contact lens of claim 2, wherein the radius of curvature of said entry surface is substantially equal to 4 cm.

8. The contact lens of claim 6, wherein the radius of curvature of said entry surface is substantially equal to 4 cm.

9. The contact lens of claim 2, wherein the value of said dihedral angle is selected from the values 32°, 28° and 23°.

10. A set of three contact lenses according to claim 2, wherein the dihedral angle of the first, the second and the third lens has a value of 32°, 28° and 23° respectively.

* * * * *